(12) United States Patent
Whipple

(10) Patent No.: US 6,319,491 B1
(45) Date of Patent: Nov. 20, 2001

(54) ANTI-SWEAT LOTION

(76) Inventor: Michael B. Whipple, 326 12th St., Unit No. B, Seal Beach, CA (US) 90740

( * ) Notice: Subject to any disclaimer, the term of this patent is extended or adjusted under 35 U.S.C. 154(b) by 0 days.

(21) Appl. No.: 09/546,965

(22) Filed: Apr. 11, 2000

(51) Int. Cl.$^7$ .................................................. A61K 7/32
(52) U.S. Cl. ........................ 424/65; 424/401; 514/772.4
(58) Field of Search .................... 424/65, 401; 514/772.4

(56) References Cited

U.S. PATENT DOCUMENTS

| | | | |
|---|---|---|---|
| 4,434,155 | * | 2/1984 | Jones et al. ............... 424/65 |
| 5,639,463 | * | 6/1997 | Kilpatrick-Liverman et al. .... 424/65 |
| 5,911,977 | * | 6/1999 | Brewster ................. 424/65 |

FOREIGN PATENT DOCUMENTS

2510364 * 9/1975 (DE) ...................................... 424/65

0154465 * 9/1985 (EP) ...................................... 424/65

* cited by examiner

Primary Examiner—Thurman K. Page
Assistant Examiner—Robert M. Joynes
(74) Attorney, Agent, or Firm—Ted Masters

(57) ABSTRACT

The present invention includes an anti-sweat lotion specifically designed for use by people suffering from hyperhidroses. In a preferred embodiment, the lotion of the present invention is a composition of the follow ingredients:

a. denatured ethyl alcohol;
b. hydrophobic silica;
c. a monoethyl ester of the copolymer of methyl vinyl ether and maleic anhydride;
d. iso-octahexacontane;
e. octamethylcyclotetrasiloxane; and,
f. hydroxypropylcelluose.

In another preferred embodiment, the octamethylcyclotetrasiloxane is replaced by decamethylcyclopentasiloxane.

4 Claims, 3 Drawing Sheets

ANTI-SWEAT LOTION

TECHNICAL FIELD

The present invention pertains to the control of perspiration, and in particular to a lotion which prevents sweat from forming on the surface of the skin.

BACKGROUND ART

Antiperspirant compositions for controlling sweating are well known in the art. For example U.S. Pat. No. 3,981,986 shows zirconium-aluminum-polyol buffered antiperspirant water soluble complexes. The complexes are satisfactory for use in any of the wide variety of conventional antiperspirant forms, including lotions, creams, roll-ons, hydro-alcoholic aerosol sprays, power-in-oil sprays, as well as manually pumped hydro-alcoholic sprays. U.S. Pat. No. 4,434,155 illustrates basic aluminum bromide compositions and methods useful as astringents or antiperspirants. The invention is superior to the conventional aluminum chlorhydroxide or basic aluminum chloride in that it is compatible with conventional aerosol propellants, and requires little additional treatment or modification before incorporation into an antiperspirant composition. U.S. Pat. No. 4,666,710 discloses antiperspirant compositions including 30% by weight of aluminum chlorhydrate, 68% by weight of ethanol, and 1.5% by weight of a long chain fatty acid, myristic acid. The invention contains relatively high levels of ethanol to promote quick drying after application to the skin, and which have good levels of antiperspirant efficacy.

As useful as the aforementioned antiperspirant compositions may be, they are not effective against excessive perspiration. Many people suffer from hyperhidrosis, which in simple terms, can be defined as overly active sweat glands stimulated by the sympathetic branch of the autonomic nervous system. This is the part of the nervous system which releases perspiration throughout the body. This is the body's natural method of cooling itself down during active periods or exposure to warm conditions. A person with hyperhidrosis experiences uncontrolled sweating and/or blushing. Those who suffer from this condition are faced with major challenges every day, and find it difficult to interact socially. They are often afraid to shake hands or perform any task which would bring them into close contact with others. First impressions play an important role in our society and in the work place. A wet clammy handshake can leave a poor and lasting impression. This can be very detrimental during that important meeting, job interview, ultimately hindering your career and relationship with others. Other symptoms of hyperhidrosis are:

General:
Washing or wiping hands constantly
Hiding hands under the dinner table
Fear of touching another person or holding hands
Exchanging money or other items in public
Avoiding manicures or pedicures
Difficulty with a neck tie
Difficulty wearing make-up
Wet hair, eyes burning due to sweat
Handling or smudging of papers
Uncomfortable playing a musical instrument
Unable to swing a golf club or baseball bat
Anxiety, difficulty concentrating Industrial:
Problems caused by prolonged use of work gloves
Handling tools and heavy objects Health Industry:
Nurses and Doctors who suffer from reactions caused by surgical gloves Sports:
As the body heats up during physical activities, sweat is produced. This can cause problems with the ability to handle balls and other sports equipment.

DISCLOSURE OF INVENTION

The present invention is directed to a novel solution to the aforementioned afflictions of hyperhidrosis. The present invention comprises a lotion that when applied to the skin, penetrates the skin's surface causing an invisible barrier. This invisible barrier keeps sweat from forming on the skin's surface, keeping it dry and comfortable for hours. The lotion protects the hands like a "liquid glove". Advantages of the composition of the present invention are that it quickly dries, and distributes over the skin evenly. Additionally, all the ingredients in the present invention are FDA approved, so it can be used safely and with confidence.

In a preferred embodiment the lotion of the present invention is a composition of the following ingredients:

a. denatured ethyl alcohol;
b. hydrophobic silica;
c. a monoethyl ester of the copolymer of methyl vinyl ether and maleic anhydride in ethanol;
d. iso-octahexacontane;
e. octamethylcyclotetrasiloxane; and,
f. hydroxypropylcelluose.

In another preferred embodiment, the octamethylcyclotetrasiloxane is replaced by decamethylcyclopentasiloxane.

Other features and advantages of the present invention will become apparent from the following detailed description, taken in conjunction with the accompanying drawings, which illustrate, by way of example, the principles of the invention.

MODES FOR CARRYING OUT THE INVENTION

The present invention is an anti-sweat lotion comprising a composition of the following ingredients:

a. ethyl alcohol (between about 90.36% and 90.56% by weight);
b. hydrophobic silica (about 8.85% by weight);
c. a monoethyl ester of the copolymer of methyl vinyl ether and maleic anhydride (about 0.1% by weight);
d. iso-octahexacontane (about 0.1% by weight);
e. octamethylcyclotetrasiloxane (about 0.1% by weight); and,
f. hydroxypropylcelluose (about 0.29% by weight).

In an alternative embodiment, the octamethylcyclotetrasiloxane is replaced by decamethylcyclopentasiloxane (about 0.1% by weight).

In a preferred embodiment, 0.2% fragrance is added to the composition. In this case, the percent of denatured ethyl alcohol is reduced from about 90.56% to about 90.36% by weight.

Provided below is a description of each of the ingredients.

Denatured Ethyl Alcohol

In a preferred embodiment the ethyl alcohol is a specially denatured alcohol in which every 100 gallons of ethyl alcohol U.S.P. includes about ½ avoirdupois oz. of brucine sulfate, N.F., and ⅛ gallon of tert-butyl alcohol. Also, in a preferred embodiment, the denatured ethyl alcohol is about 200 proof. Denatured ethyl alcohol of this formula is available as Specially Denatured Alcohol 40-2 from:

REMET CORPORATION
16511 Knott Ave.
La Mirada, Calif. 90638
(714) 739-0171

Hydrophobic Silica

Figure 1:
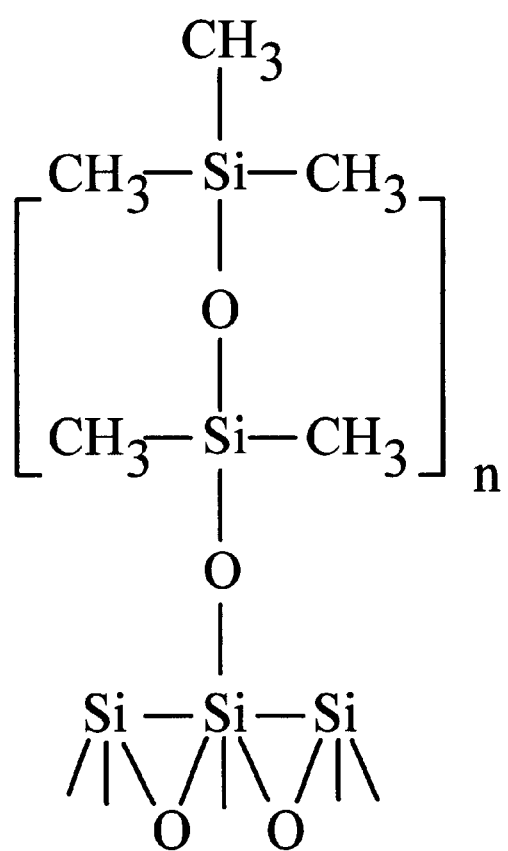
FIG. 1 is a diagram of the surface chemistry of hydrophobic silica.
Figure 2:
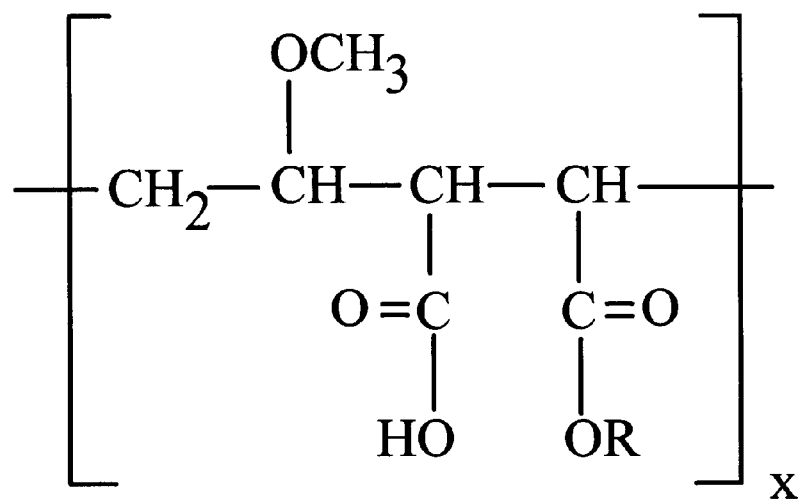
FIG. 2 is a diagram of the molecular structure of monoethyl ester of the copolymer of methyl vinyl ether and maleic anhydride.

The hydrophobic silica comprises treated fumed silica which is a high-purity silica which has been treated with a dimethyl silicone fluid. The treatment replaces many of the surface hydroxyl groups on the fumed silica with a polydimethyl siloxane polymer. This treatment makes the silica extremely hydrophobic. During treatment the surface of the silica is completely coated with the silicone fluid agent. The silicone fluid reacts with the surface hydroxyl groups. The surface chemistry of the treated silica is shown in FIG. 1. The treated silica does not thicken liquid systems by hydrogen bonding, as do untreated grades. Rather, it relies on the interaction of its modified surface chemistry with the liquid system. In a preferred embodiment, the hydrophobic silica has the appearance of fluffy white powder, a bulk density of about 3.5 lb/ft$^3$, and a specific gravity of about 1.8 g/cm$^3$. Hydrophobic silica is available as CAB-O-SIL® TS-720 from:

Cabot Corporation
Cab-O-Sil Division
700 E. U. S. Highway 36
Tuscola Ill. 61953
(217) 253-3370
(217) 253-4334 fax Monoethyl Ester of the Copolymer of Methyl Vinyl Ether and Maleic Anhydride in Ethanol SDA-40A This ingredient is a monoester resin of monoalkyl esters of poly(methyl vinyl ether/maleic acid. The poly(vinyl methyl ether) is a flexible film former, while the maleic anhydride is a hard polar monomer which contributes bonding strength. Neutralization of the copolymer's acid group increases the water solubility of the resin and plasticizes the copolymer, enabling easy removability by shampooing. In a preferred embodiment this ingredient is an ethyl ester of PVM/MA Copolymer, supplied in 50% active ethanol, and has the appearance of a viscous liquid. FIG. 2 shows the molecular structure. This ingredient is available as GANTREZ® ES-225 from:

International Specialty Products
767 North Thompson Ave.
Bound Brook, N.J. 08805
(732)271-0111

Iso-Octahexacontane

Iso-octahexacontane is a $C_{68}$ aliphatic hydrocarbon, whose CTFA adopted name is Polyisobutene, having the appearance of a clear, viscous liquid, and a CAS# of 9003-29-6. Iso-Octahexacontane is available as PERMETHYL® 104A from:

Presperse Inc.
141 Ethel Road West
Piscataway, N.J. 08854
(732) 819-8009

Octamethylcyclotetrasiloxane

Figure 3:
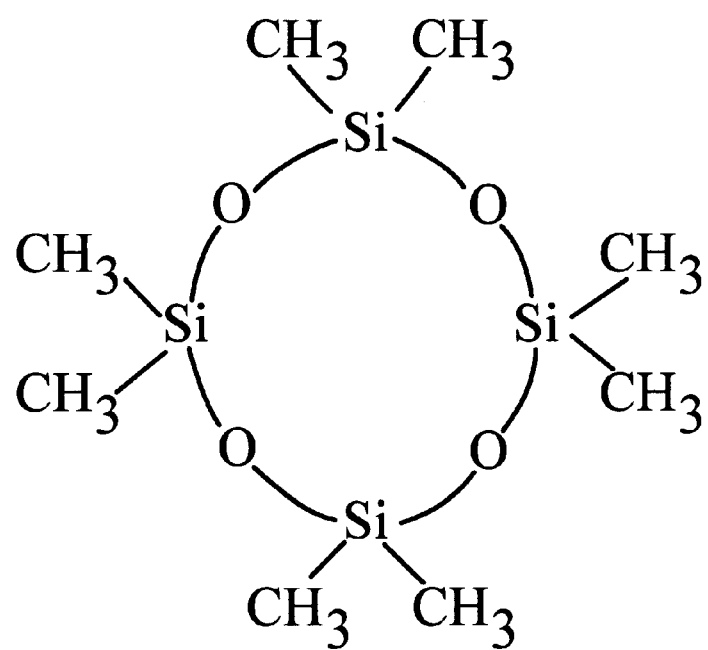
FIG. 3 is a diagram of the chemical structure of octamethylcyclotetrasiloxane.

Octamethylcyclotetrasiloxane is one of a polydimethycyclosiloxane family of low viscosity silicone fluids designed for use as an ingredient in a wide range of cosmetic and personal care product formulations. They feature high compatibility with many cosmetic ingredients and good solubility in most anhydrous alcohols and in many cosmetic solvents. These products are clear, odorless, nongreasy and nonstringing, and have a long history of use in cosmetic preparations. As base fluids or as transient carriers, they allow good spreading and easy rub-out. Volatile silicones provide these properties plus the detackification properties of a low viscosity silicone, but evaporate leaving essentially no residue. They reduce surface tension, aid in formula spreading, and promote leveling of solid pigments. The family of fluids can be used alone, blended with each other, or blended with other cosmetic fluids to provide a fluid base for a variety of cosmetic ingredients. When used as a carrier in antiperspirants and deodorants, these fluids leave a dry feel and does not cool the skin when they evaporate. The chemical structure of octamethylcyclotetrasiloxane is shown in FIG. 3. Octamethylcyclotetrasiloxane is available as Dow Corning® 244 Fluid from:

Dow Corning Corporation
Midland, Mich. 48686-0994
(517)496-6000

Decamethyalcyclopentasiloxane

Figure 4:
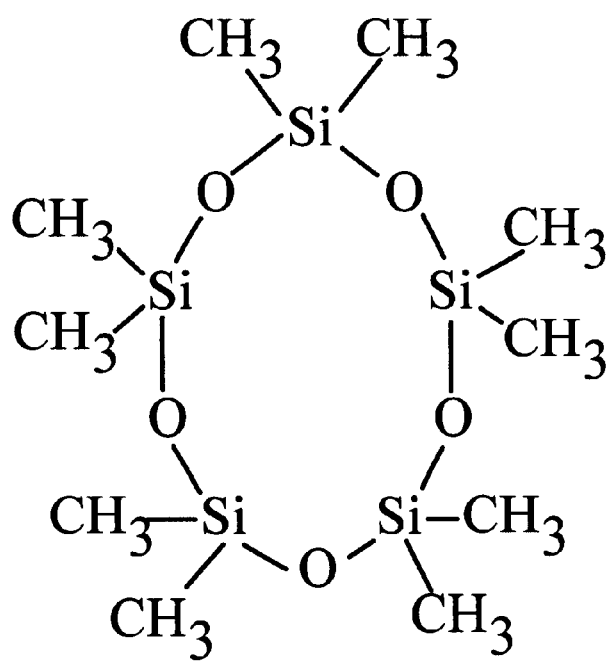
FIG. 4 is a diagram of the chemical structure of decamethylcyclopentasiloxane; and, FIG. 5 is a diagram of the chemical structure of hydroxypropylcelluose.

Decamethyalcyclopentasiloxane is another member of the polydimethycyclosiloxane family that can be substituted for the previously cited octamethylcyclotetrasiloxane, and is available as Dow Corning® 245 Fluid for Dow Corning as above. The chemical structure of decamethyalcyclopentasiloxane is shown in FIG. 4.

Hydroxypropylcelluose

Figure 5:
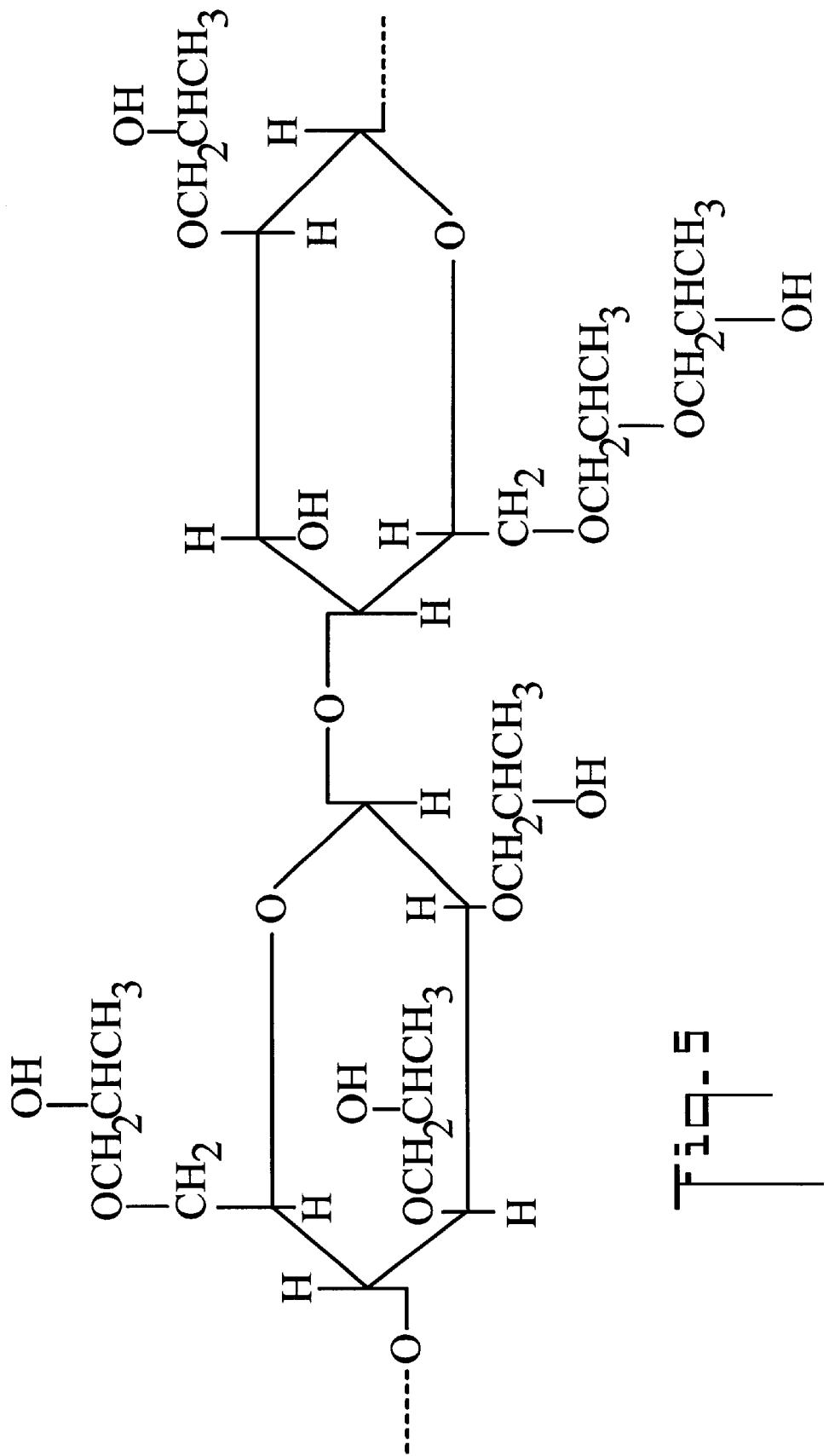

Hydroxypropylcelluose (HPC) is a nonionic water-soluble cellulose ester with a versatile combination of properties. It combines organic solvent solubility, thermoplasticity, and surface activity with the thickening and stabilizing properties of other water-soluble cellulose polymers. It is used in a wide variety of applications, including food, cosmetics, pharmaceuticals, coatings, adhesives, extrusions, and moldings, paper, paint removers, encapsulations, inks, and many other applications requiring a film-former, thickener, stabilizer, suspending agent, film barrier, thermoplastic, or protective colloid. Hydroxypropylcelluose (HPC) has the appearance of an off-white, tasteless powder. The chemical structure of hydroxypropylcelluose is shown in FIG. 5. Hydroxypropylcelluose is available as Kucel® from:

Hercules Incorporated
Aqualon Division
Hercules Plaza
1313 North Market St.
Wilmington, Del. 19894-001
(302) 594-5000

In terms of manufacture, the hydroxypropylcelluose is first dissolved in the denatured ethyl alcohol, and then the other ingredients are added and blended in the order recited above.

The preferred embodiments of the invention described herein are exemplary and numerous modifications, variations, and rearrangements can be readily envisioned to achieve an equivalent result, all of which are intended to be embraced within the scope of the appended claims.

I claim:
1. An anti-sweat lotion composition, comprising:
   a. denatured ethyl alcohol;
   b. hydrophobic silica;
   c. a monoethyl ester of the copolymer of methyl vinyl ether and maleic anhydride;
   d. iso-octahexacontane;
   e. octamethylcyclotetrasiloxane; and,
   f. hydroxypropylcelluose.
2. An anti-sweat lotion composition, comprising:
   a. denatured ethyl alcohol;
   b. hydrophobic silica;
   c. a monoethyl ester of the copolymer of methyl vinyl ether and maleic anhydride;
   d. iso-octahexacontane;
   e. decamethyalcyclopentasiloxane; and,
   f. hydroxypropylcelluose.
3. An anti-sweat lotion composition, comprising:
   a. denatured ethyl alcohol between about 90.36% and 90.56% by weight;
   b. hydrophobic silica about 8.85% by weight;
   c. a monoethyl ester of the copolymer of methyl vinyl ether and maleic anhydride about 0.1% by weight;
   d. iso-octahexacontane about 0.1% by weight;
   e. octamethylcyclotetrasiloxane about 0.1% by weight; and,
   f. hydroxypropylcelluose about 0.29% by weight.
4. An anti-sweat lotion composition, comprising:
   a. denatured ethyl alcohol between about 90.36% and 90.56% by weight;
   b. hydrophobic silica about 8.85% by weight;
   c. a monoethyl ester of the copolymer of methyl vinyl ether and maleic anhydride about 0.1% by weight;
   d. iso-octahexacontane about 0.1% by weight;
   e. decamethyalcyclopentasiloxane about 0.1% by weight; and,
   f. hydroxypropylcelluose about 0.29% by weight.

* * * * *